United States Patent [19]

Newton

[11] 4,284,495

[45] Aug. 18, 1981

[54] COATING APPARATUS AND METHOD

[76] Inventor: William A. Newton, Suite 238, 300 East Bldg., 300 31st St., North, St. Petersburg, Fla. 33713

[21] Appl. No.: 121,895

[22] Filed: Feb. 15, 1980

Related U.S. Application Data

[63] Continuation-in-part of Ser. No. 101,758, Dec. 10, 1979.

[51] Int. Cl.$^3$ .............................................. B07C 5/342

[52] U.S. Cl. ..................................... 209/3.1; 209/932; 356/72; 250/222 PC; 34/57 R; 159/1 A; 159/43 R; 159/DIG. 11; 424/3; 427/4

[58] Field of Search ................................. 209/3.1-3.3, 209/552, 576, 577, 578, 579, 932, 906, 3, 2, 127 R, 127 A, 127 C; 356/39, 72, 73, 335-343, 440-442, 246; 324/71 CP; 235/92 PC; 250/222 PC, 573, 574, 576; 34/57 R; 159/1 A, 43 R, DIG. 11; 424/3; 427/4; 118/64

[56] References Cited

U.S. PATENT DOCUMENTS

| | | |
|---|---|---|
| 2,020,719 | 11/1935 | Bottoms . |
| 3,300,868 | 1/1967 | Anderwert . |
| 3,380,584 | 4/1968 | Fulwyler . |
| 3,466,209 | 9/1969 | Leveskis . |
| 3,467,617 | 9/1969 | Weichselbaum et al. . |
| 3,498,860 | 3/1970 | Pickett . |
| 3,546,334 | 12/1970 | Lerner et al. . |
| 3,710,933 | 1/1973 | Fulwyler et al. . |
| 3,888,017 | 6/1975 | McBride . |
| 3,891,327 | 6/1975 | Welch . |
| 4,120,991 | 10/1978 | Ornstein et al. . |

*Primary Examiner*—Joseph J. Rolla
*Attorney, Agent, or Firm*—William A. Newton

[57] ABSTRACT

Disclosed is an evaporator apparatus and method for encapsulating individually isolated particles with a coating material wherein uniformally sized droplets, normally having no more than one particle, are formed from a mixture of the coating material, the suspended particles, and a carrier liquid; the droplets then being charged, steered by an electrostatic arrangement of a tubular electrode and at least one other electrode so as to be retained in a temperature controlled, predetermined area for a sufficient time period to allow the complete evaporation of the carrier liquid.

21 Claims, 6 Drawing Figures

COATING APPARATUS AND METHOD

CROSS REFERENCE TO RELATED APPLICATION

This application is a continuation-in-part of an earlier filed application, Ser. No. 101,758, filed on Dec. 10, 1979.

FIELD OF THE INVENTION

The present invention is related to evaporators for depositing a coating around relatively small particles.

DESCRIPTION OF THE PRIOR ART

In the medical field, there are several techniques used for preparing and preserving a thin, stained tissue specimen for microscope observation. In one technique, the specimen is mounted on a microscope slide; the specimen is coated with a resin in solution; a cover glass is mounted over the specimen on the microscope slide; and the solvent is evaporated in a warm environment. Additionally, the evaporation of the solvent hardens the resin; binds the cover glass to the microscope slide; and lessens optical interference caused by residual solvent. Additionally, the resin acts to preserve the specimen. Examples of this technique are illustrated in U.S. Pat. Nos. 3,466,209 and 3,467,617. Such resinous compositions are commonly known as mounting mediums or mountants.

Due to several drawbacks of the above described technique, there evolved a technique wherein the specimen is coated with a mountant in the form of a low-volatile polymerizable material, such as liquid acrylic reactomers, in combination with an ultraviolet light-sensitive catalyst. The polymerizable material is then exposed, normally through the cover glass or microscope slide, to ultraviolet radiation to polymerize the mountant into a hard, transparent coating. Such a technique is illustrated in U.S. Pat. Nos. 4,120,991 and 3,891,327. This encapsulating coating preserves the specimens indefinitely.

In both of the above described techniques, pressure of the cover glass is used to dispense the mountant over the specimen in a sufficiently thin layer for proper microscope examination. None of the techniques have been successfully applied to individually isolated cells. Biological cells, due to their small size, can be readily washed off the microscope slide by the application of the mountant and are very susceptable to damage through drying prior to the application of the mountant. In addition, the normal problems, such as entrapped air bubbles beneath the cover glass, become more of a hinderance. The use of the pressure of the cover glass for generating a uniformally thin coating of mountant, be it a resin solution or a polymerizable material, frequently provides too thick or too thin of a layer of mountant. Moreover, the evaporation of a resin solution from between the slide and the cover glass is very slow, and frequently leaves residual solvent which creates optical interference.

It is a common practice to prepare and preserve stained, individually isolated cells for microscope examination by applying thereto fixative and preservation compositions. Such compositions are disclosed in U.S. Pat. No. 3,546,334, wherein an opaque, temporary protective coating is applied to a smear of blood cells. This coating is removed, typically by washing, prior to microscope examination.

In many art areas wherein small particles are involved, there is a need for surrounding the individual particle with a solution and thereafter evaporating the solvent so as to encapsulate the individual particle in a thin coating of solute.

Various spray drying techniques are used in the art wherein droplets are frozen and then sublimated, as shown by U.S. Pat. No. 3,300,868 to Anderwert. Moreover, solidification of a solute in an initially liquid, refrigerant gas was attempted in U.S. Pat. No. 2,020,719 to Bottoms. Formation of initially liquid, solute oxidizer particles was attempted by spray freezing in U.S. Pat. No. 3,888,017 to McBride. However, these patents do not deal with individually isolated particles wherein certain acts, such as coating, sorting, or parameter detection of the present invention, are performed thereon while suspended. Moreover, these techniques require lengthy chambers and generally require freezing and low pressures. Moreover, control of very small particles therein is not possible. As spray droplets and residues resulting therefrom decrease in size they generally possess low momentum and thus, at best, must usually require an air current to convey the fine particles to their desired destination. For example, fine particles of 20 microns in diameter or less settle very slowly in quiescent air, and if sufficiently small, may become at least temporarily suspended. Moreover, such fine particles follow any eddies of air or other air movements.

SUMMARY OF THE INVENTION

The present invention relates to an evaporator apparatus and method wherein a droplet forming means forms a plurality of uniformly sized droplets of a liquid mixture, which includes a coating material and a liquid carrier, and normally no more than one individually isolated particle. The droplets leave the droplet forming means with an initially linear trajectory and are charged by a charging means. Electrode means are provided for generating electrostatic forces for positioning the particles substantially along a center axis and for moving the particles along the center axis at a rate of movement to allow evaporation of the carrier liquid of the droplets within a limited predetermined region. The evaporation of the carrier liquid leaves the particle encapsulated in a film of the coating material. The electrode means includes a tubular electrode, which is positioned to receive the droplets in its interior and is centered on the center axis, and a second electrode, which is positioned at one end of the tubular electrode. A potential difference is provided between the tubular and second electrodes so as to apply to the tubular electrode a charge of the same polarity as that of the droplets.

If the center axis is vertically aligned, the second electrode is positioned to shape the electrostatic forces to have a force component parallel to the center axis for initially retarding the particles downward movement along the center axis, thereby counteracting the gravitational force. For relatively small particles, a third electrode can be positioned at the other end of the tubular electrode to assist the particles' movement in the lower portion of the tubular electrode after evaporation is completed or nearly completed. If the center axis is horizontally aligned, then the second electrode is normally used to assist the movement of the particles, thereby overcoming air resistance. In either case, the tubular and second electrodes are aligned and configured for shaping the electrostatic field to provide an inwardly directed, radial force component for substantially aligning the particles with the center axis or a predetermined trajectory or plane from which they can be collected.

By virtue of this invention, the entire evaporation process can be maintained in a reasonable sized region with heat input, if needed, being limited to that region and with the use of volatile carrier liquids that do not have to be highly volatile. The individually isolated particles can be encapsulated with a relatively thin and uniform coating of a predetermined amount of coating material.

BRIEF DESCRIPTION OF THE DRAWINGS

Further objects and advantages of the present invention will become apparent as the following description proceeds, taken in conjunction with the accompanying drawings in which.

DETAILED DESCRIPTION OF THE PREFERRED EMBODIMENTS

Figure 1:
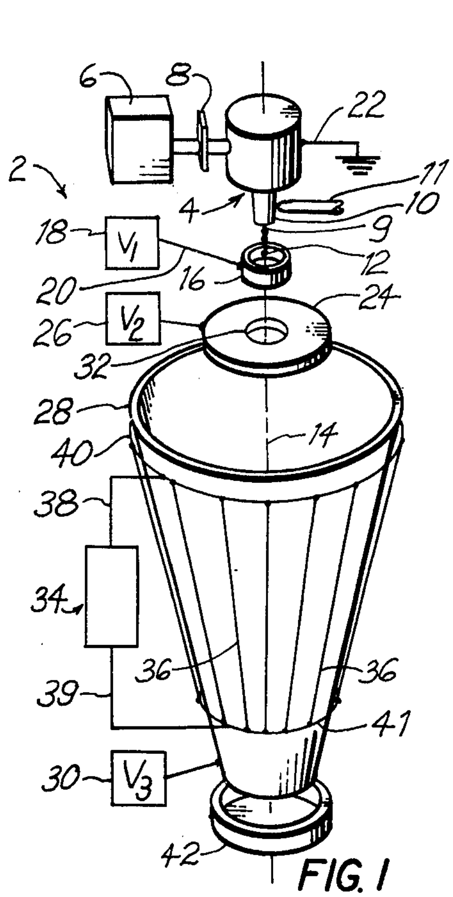
FIG. 1 is a perspective view of the evaporator apparatus of the invention.

Referring to FIG. 1, there is disclosed an evaporator apparatus, which is generally indicated by numeral 2. The apparatus 2 includes a conventional droplet forming means 4, preferably of the type disclosed in U.S. Pat. No. 3,380,584 to Fulwyler and U.S. Pat. No. 3,710,933 to Fulwyler et al. As in these well known prior art arrangements, a dilute solution of particles is suspended in a liquid and feed from a fluid container 6, through a strainer 8, to the droplet forming means 4. The strainer 8 is employed to stop particles of a gross size from clogging the system, while allowing particles within a size range of interest to pass therethrough.

The container 6 has therein a liquid mixture of a coating material, which can be a liquid, semi-solid or solid, and a carrier liquid, which can be a solvent or a dispersant. As will be shown by the hereinafter described examples, the most common uses of the invention will involve a solution; however, the invention can also be used with colloidal suspensions and, assuming for example prior stirring and proper preparation, even with relatively coarse suspension. Hence, the term "liquid mixture" is intended to cover mixtures extending from homogeneous to heterogenous, with the coating material, whether solid or liquid, being dissolved or suspended therein. In one implementation of the apparatus 2, biological cells are suspended in the liquid mixture so as to be subsequently encapsulated with the coating material. However, the apparatus 2 can be used with any granular material wherein the grains or particles can be separated and suspended, at least temporarily, in a liquid, for example, by using well known stirring or ultrasonic techniques. As will become apparent, the carrier liquid must be substantially more volatile than the coating material, which is normally relatively non-volatile. However, due to the electrostatic field arrangement, sufficient time is provided for complete non-turbulant evaporation to permit the use of carrier liquids that are no more volatile than a saline solution.

A flow stream, in the form of a liquid jet 9, is formed within a nozzle 10. In a well known manner, the nozzle 10 is coupled to vibration means (not shown) by means of a coupling rod 11. Vibrations imparted to the nozzle 10 produce minute disturbances or bunching on the liquid jet 9. By producing these disturbances at a proper frequency, determined by the diameter, viscosity and velocity of the jet 9, the bunching grows in size by surface tension, until the jet 10 is broken into evenly spaced, uniformly sized droplets 12. As is known in the art, the dilution of the particle sample introduced into the container 6, the size of the droplets 12, and the frequency of the ultrasonic mechanical disturbances conveyed by the coupling rod 11 are chosen so that, on a statistical basis, each droplet 12 normally contains no more than a single isolated particle, although some droplets 12 do not contain any particles. Typically, for particles having diameters from 1 to 75 microns, droplets 12 having diameters from 75 to 150 microns are desirable. Although the velocity of the jet 9 can be readily varied from 0.1 to 15 meters per second, due to the time required for hereinafter described evaporation, velocities toward the low end of this range are desirable. To those skilled in the art, it will be obvious that the above described set of conditions can be varied substantially, depending upon the intended usage of the apparatus 2. These droplets 12 have an initial linear trajectory along the center axis 14. Subsequently, the droplets 12 are charged by a conventional charging collar electrode 16, in the same manner as illustrated in the two above-mentioned patents. More specifically, a potential is applied between the nozzle 10 and the collar electrode 16 by a first voltage source 18, by use of a pair of leads 20 and 22. In this first mode of operation to be described, a constant voltage is applied by the voltage source 18 to the collar electrode 16 so that all droplets 12 are uniformly charged. Hence, the droplets will repel each other and not coalesce. In the embodiment of FIG. 1, an ion producing solute is normally included in the mixing liquid, examples of which will be provided hereinafter. Not only does this provide for greater magnitudes of charging for each droplet, in instances where biological cells are being processed, chances of cell rupture can be minimized.

Figure 2:
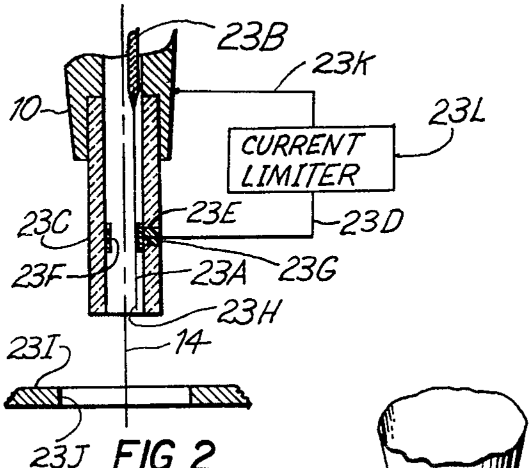
FIG. 2 is an enlarged fragmentary view of a modification to the embodiment of FIG. 1.

Referring to FIG. 2, a well known alternative way of charging the droplets is shown. Instead of the collar electrode 16 of FIG. 1, a very sharp tungsten needle is used. The tungsten needle 23A is mounted at one end by a glass filament 23B, which in turn is attached to the casing of the droplet forming means 4. The end of the nozzle 10 comprises a glass portion 23C. A high voltage connection is made with the needle 23A by way of a conductor 23D, which passes through a slot 23E formed in the glass portion 23C and connects to a small nickel tube 23F which is mounted inside the glass portion 23C. The needle 23A is soldered to the tube 23F. A silicone rubber sealant 23G fills the slot 23E, sealing it off. The tip 23H of the needle 23A is positioned at the outlet of the nozzle 10. A grounded disk electrode 23I, (partially shown) with an aperture 23J, is positioned below the nozzle 10 and acts as an electrostatic shield. The electrode 23I, which can also be used in the embodiment of FIG. 1, can be expanded, if desired, to enclose the nozzle 10. A high potential, such as 10,000 volts, is applied to the needle 23A. Depending upon the polarity of the applied high potential, the high field at the very sharp tip 23H will emit electrons into the liquid jet 9 or field ionize the jet. The charged jet 9, in the same manner as previously described, breaks up into uniformally charged droplets. The amount of charge injected into the liquid jet 9 is determined by the current in the tungsten needle circuit 23K, which can be varied and controlled by a conventional current limiter 23L. In general, this droplet charging arrangement is of conventional design.

With the induction type charging, charges in the order of $10^{-12}$ coulombs can be uniformally applied to each droplet of, for example, a 1 to 2% saline solution. An equal or greater amount of charge can be applied by the field emission and field ionization charging methods of the tungsten needle. The use of tungsten needle approach is preferable to the induction charging whereever it can be used, i.e. for charging insulating liquids. A few illustrative insulating liquids, with low charge relaxation time constants and moderate volatility, would be toluene, xylene, and benzene. Examples of highly volatile carrier liquids would be Freon. Water is generally a poor insulating liquid. Where aqueous solutions or solutions of ion producing salts are used, induction type charging should be used. Induction charging has the disadvantages of the residual ion-producing solutes interfering to a limited degree with some types of particle coating materials and decreasing vapor pressure of the carrier liquid as ion-producing solute concentrations increase as evaporation proceeds. The tungsten needle approach does not have these disadvantages, but cannot be used with, for example, saline solutions that are used to prevent rupture of suspended biological cells.

Other means of charging the droplets will be obvious to those skilled in the art. Examples of other techniques would be corona charging, ion and electron beam charging, radiation charging, and a spray chamber filled with an ionized gas.

In FIG. 1, a metal ring electrode 24 is axially aligned with the center axis 14 below the collar electrode 16 and is charged with a voltage from a second voltage source 26 having a sign opposite to the charged droplets 12 and the same as that of the voltage applied to the collar electrode 16. A metal, annular tubular electrode 28 is axially aligned with the center axis 14 and has a voltage applied by a third voltage source 30 which is opposite in sign to the voltage applied to the ring electrode 24. Hence, due to their momentum and trajectory, the droplets pass through an aperture 32 of the ring electrode 24 and are attracted by the ring electrode 24, while being repelled by the tubular electrode 28. Hence, an electrostatic field, which is radially symmetric about the center axis 14, retards the downward velocities of the droplets within desired ranges.

Depending primarily on the volatility of the carrier liquid, the interior of the tubular electrode 28 is maintained within desired temperature ranges. The term "temperature regulating means" will be used herein to include, as shown in the preferred embodiment, heat input means 34 where heat flux must be inputted to raise temperatures, to achieve the desired rates of evaporation. This term is also meant to cover a conventional heat exchanger arrangement where temperatures must be reduced to achieve the desired rates of evaporation. For most of the moderately volatile carrier liquids illustrated herein, the interior of the tubular electrode 28 is raised in temperature by the heat input means 34 to, for example, temperatures of 65° C. Generally, it has been found desirable to keep the temperature below the boiling point of the carrier liquid, so as to avoid turbulent evaporation that can remove coating material, and if present, ion producing solutes. Although not the preferred implementation, it is contemplated that the invention can be used with highly volatile carrier liquids, such as Freon. However, to maintain temperatures below the boiling point of the highly volatile carrier liquids, refrigeration in the form of a heat exchanger would be required. In the preferred implementation, moderately volatile liquids, having boiling points in the vicinity of 80°-110° C., require the input of heat flux in a continuous manner, as provided by heat input means 34. Limitations on the temperature ranges will be discussed in more detail hereinafter. The heat input means 34 is shown having a heat radiating emitter in the form of a plurality of electrically interconnected heating filaments 36, which are disposed in adjacent, spaced-apart relationship to the outside of the tubular electrode 28. Typically, the heat input means 34 would include a power source electrically connected to the heating coils 36 through a pair of conductors 38 and 39 and a pair of loop conductors 40 and 41. Optionally, primarily for the sake of safety, the heating coils 36 can be surrounded by a housing (not shown) formed of an electrical and thermal insulating material, such as fiberglass.

Due to the radially symmetrical field, the droplets, which eventually become particles, remain substantially centered on center axis 14. As the droplets lose mass and proceed down the tubular electrode 28, they experience a decreasing, electrostatic retarding force. Consequently, the decreasing repelling force of the electrostatic field can be at least somewhat tailored to compensate for the decreasing weight of the droplets, thereby providing for a controllable throughput of particles. The potential difference between the first and second voltage sources 18 and 30, i.e. the tubular electrode 28 and the collar electrode 16, can vary, for example, between 5,000 volts and 25,000 volts, depending upon the operating parameters.

As the carrier liquid evaporates, the non-volatile coating material forms a relatively thin film or coating about the particle. Since the droplet forming variables have been set so that normally no more than one particle is in each droplet, each individually isolated particle will be coated by a predetermined amount of coating material. The ions, which remain on the surface of the evaporating droplet, are retained during the controlled evaporation, so that there is preferably no loss in charge. Consequently, the total charge on the particle is substantially the same as that applied to the original droplet. However, the present invention is operable even with substantial charge loss as evaporation proceeds, since smaller droplet weights and greater air drag require less retarding electrostatic forces. The ions, including salt ions, will, after drying be disposed on the outside of the coating material and will not substantially interfere with the coating process. With sufficiently low concentrations of the coating material, the residual film about the particle can be made very thin, such as, for example, 0.01 microns. Prior to the particle's exit from the tubular electrode 28, all the carrier liquid has evaporated. The particles then land in a particle collector 42, formed on a non-conducting material. Examples of various coating material-carrier liquid combinations will be provided subsequently.

Figure 3:
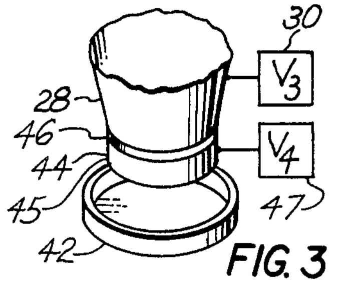
FIG. 3 is an enlarged fragmentary view of another modification to the embodiment of FIG. 1.

FIG. 3 shows a modification of the embodiment of FIG. 1 wherein a third electrode 44, in the form of a ring-like, circular electrode 45, is mounted below the tubular electrode 28 and separated therefrom by a circular band 46 formed of a non-conducting material. The third electrode 44 is held at ground potential or, if desired, at a potential of opposite sign to the tubular electrode 28, by a fourth voltage source 47. The ring-like electrode 45 is added to the apparatus 2 so as to assist small particles, such as, for example, 20 micron diameter or smaller to proceed through the tubular electrode 28 and the ring-like electrode 45; thereby preventing the small particles from proceeding too slowly, becoming suspended, or reversing direction and proceeding upward. Generally, for larger particles, the third electrode 44 is not needed. Consequently, the progress of the droplets along the center axis 14 is initially retarded by a repelling electrostatic force while the droplet is heavy so as to allow sufficient time for the completion of the desired evaporation and then are accelerated. This accelerating electrostatic force shoots the particle through the center of the ring-like electrode 45.

Figure 4:
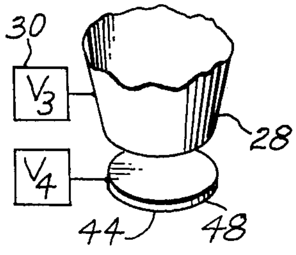
FIG. 4 is an enlarged, fragmentary view of yet another modification to the embodiment of FIG. 1.

FIG. 4 shows another modification of the embodiment of FIG. 1. Referring to FIG. 3, very small, low momentum particles, such as 1 micron diameter particles, can, at least in limited numbers, follow the lines of force, and become adhered to the ring-like electrode 45. The lighter and more off-centered the particles, the more likely this will happen. In those applications wherein higher collection rates are desired, the third electrode 44 takes the form of a disk electrode 48, as shown in FIG. 4. The particles can be readily removed with an extremely high collection rate from the disk electrode 48. Also, a thin non-conducting tape (not shown) mounted on a pair of reels, can be moved across the top of the disk electrode 48 to continuously catch the descending particles.

Figure 5:
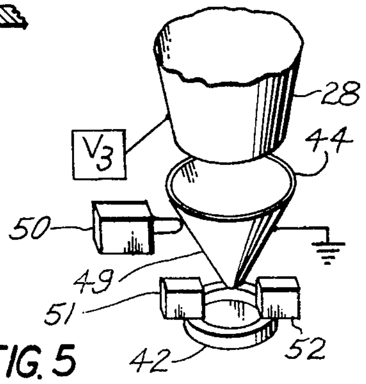
FIG. 5 is an enlarged fragmentary view of yet another modification to the embodiment of FIG. 1.

FIG. 5 illustrates another embodiment of FIG. 1 wherein the third electrode 44 takes the form of a metal funnel 49, which is normally held at ground potential. Preferably, in this embodiment, the particles are positively charged. The particles will initially be attracted to the funnel 49 by their image force and, depending upon their conductivities, i.e., particle and particle-funnel contact resistances, may immediately lose their charge and slide down the funnel 49 or, if they have a high relaxation time, may adhere to the funnel for a time dependent on the relaxation time. Also, some particles may have a sticky adhering surface, thereby needing the assistance of a mechanical vibrator 50 to detach the particles. Subsequently, the particles are collected in the particle collector 42. Optionally, numerous optical tests commonly performed on aerosols and like airbourne particles can be performed on the particles as they fall from the funnel 52. The apparatus for the optical tests are shown by the placement of a light source 51, typically a laser beam, and at least one light detector 52, typically a photomultiplier cell, on opposed sides of the particle stream. This arrangement presupposes that the particles are of sufficient size to settle in the gaseous medium of a predetermined viscosity and pressure, so as to land in the particle collector 42. Optical methods normally measure forward scattered light, at an angle to the incident beam and/or if detector 52 or a second detector is properly positioned, backscattered light. The specific structure and arrangements of the optical test apparatus are well known in the aerosol art. However, the present invention allows the particles to be confined in a narrow stream emanating from the funnel 49 with, if desired, a minimal amount of particle coincidence.

EXAMPLE 1

One application of the invention is for applying a relatively uniform, thin layer of liquid, polymerizable material to a particle, such as, but not necessarily, a biological cell. Although biological cells have been selected to describe this technique, it should be understood that a wide range of different types of small particles, generally from 1 to 75 microns in diameter can be coated by this technique. Suitable solutions of mountants are disclosed in U.S. Pat. No. 4,120,991 to Ornstein et al. A low volatile, liquid acrylic reactomers and an ultraviolet-light sensitive catalyst are suspended in a volatile solvent. To provide a relatively thin film, the acrylic reactomers must be in relatively low concentrations, such as 0.5 percent by volume. The solvent is allowed to completely evaporate while the particles are airbourne, leaving a thin layer of mountant. Preferably, after the coated particles land in the collector, they are exposed to ultra violet radiation, such as a fluorescent black-light lamp to create particles with a hardened, optically clear, protective coating. The polymerization of the films is accomplished in a conventional manner and is not part of this invention. With biological cells, they can be stained and fixed prior to being suspended in the solvent. Acdeptable volatile solvents are, for example, xylene, toluene and Freon. The mountant can be a low-volatility, low-viscosity liquid acrylic reactomers such as methacrylates, acrylates and vinyls and a catalyst sensitive to ultraviolet light, such as benzoin, benzoin ethers, acetophenones or Michler's ketone. It will be obvious to those skilled that there can be numerous solutions of polymerizable material that can be used with the invention. Moreover, numerous types of minute particles of varying composition and size can be coated in the present invention.

EXAMPLE 2

In another application of the present invention, a solution of a resin mountant is used. A variety of conventional resins, which are commonly used to provide a transparent, hardened coating for tissues, can be used in the invention, some of which are illustrated in U.S. Pat. No. 3,891,327 to Welch. A few illustrative examples would be u-pinene resin, Canada balsam and various known synthetic resins. Generally, the mountant is dissolved in sufficient concentrations in the solvent to provide a thin, relatively uniform film of mountant about the particle. The removal of the solvent by evaporation, while the particles are airbourne, hardens the mountant and provides a relatively transparent coating. This technique is particularly useful for biological cells, which normally range from 7 to 50 microns. For these size ranges of cells, a concentration of Canada balsam of, for example, 1% by volume of the solution is adequate for providing a thin coating.

EXAMPLE 3

Biological cells, normally stained, can be coated with a fixative and protective composition. The application of this protective coating prevents the cells from drying after the water of the droplet has been removed therefrom. Drying can prevent useful microscope examination of the cells. One example of a fixative and protective coating is illustrated in U.S. Pat. No. 3,546,334 to Lerner et al., and comprises an alcohol, a polyalkylene glycol and a ketone. The alcohol and the ketone evaporate off, while the particles are in the air, leaving a thin film of polyalkylene. However, prior to viewing under a microscope, the coating must be washed off.

EXAMPLE 4

In another application of the invention, the apparatus 2 can be used to apply a coating of adhesive to the particle so as to secure the same to a substrate, such as a microscope slide or moving tape which will be used in subsequent microscope examination. In this application, the suspension solution can comprise a volatile solvent, such as, for example, xylene, and a non-volatile adhesive solute, such as, for example, an acrylic resin. The acrylic resin may be, for example, a polyacrylate, a polymethacrylate or copolymers of the same. Typically, the acrylic resin will sufficiently coat, for example, the average sized cell initially disposed in a 100 micron diameter droplet when comprising 0.5 percent of the solution by volume. Combinations of solvents and solutes for adhering the tissue samples to surfaces of substrates are known in the art as shown by U.S. Pat. No. 3,498,860 to Pickett and are readily usable in this invention. This application is particularly useful for adhering dried biological cells to a substrate. For example, when the unbound water of the cell has been substantially replaced with a volatile liquid, normally the volatile solvent of the suspension solution, the cell will be dried during evaporation, leaving a very light particle with its natural sticky exterior being eliminated. Hence, the thin layer of adhesive solute allows for the dried cells to adhere to the substrate. It is also contemplated that the adhesive coating can be used in combination with the heretofore-mentioned resin protective coatings of the type that are not polymerized after application. Other types of particles could be adhered to other surfaces using this technique.

Referring to the examples in general, where induction charging is used, the ion producing solutes or electrolytes for the non-aqueous, volatile solvents contemplated by the present invention are well known. The mechanism of ion formation requires that the solvent be polar enough to cause a dissolved salt to dissociate into ions. In addition, the particles being processed must not be soluble in the solvent or solutes. Some illustrative ion solutes would be ammonium thiocyanate in an amount of 10% by volume in toluene, and lithium chloride in an amount of 2% by volume of benzene. It is contemplated that with some coating solutes of low volatility, water can be used as a solvent with the normal 1 to 2% of sodium chloride for the ion solute. If Freon is used, then ammonium thiocyanate in the amount 4% by volume of fluoroacetic acid can be used.

Referring to the examples in general, there is no delay in applying the mountant, therefore eliminating any possibilities of drying of, for example, biological cells. Likewise, there is no problem with entrapped air bubbles commonly occuring with the prior art's use of glass slides for the specimen.

Referring to the examples in general, evaporation can be readily completed, without leaving any troublesome residue of liquid carrier and, depending upon the liquid carrier, with relatively low heat fluxes. This is due the electrostatic field arrangement of the invention retaining the droplets in a limited predetermined region, for example a meter or less in length, so as to allow complete, controlled evaporation at moderate temperatures. The desirable temperatures will primarily depend upon the temperature sensitivity of the particles and the volatility and boiling point of the carrier liquid. For biological materials, it is frequently desirable not to exceed 65° C. It is contemplated that higher temperatures can be used with temperature insensitive particles. However, for each carrier liquid there is a temperature whereat evaporation will proceed so rapidly and be so turbulent that at least some of the cooling material and charge will be removed by the rapidly escaping vapor. Depending upon the application and the predictability of the lost solutes, this can be undesirable. Moreover, at very high temperatures, miscible, multi-component droplets can actually explode, due to internal pressure buildup caused by volatile solvent being trapped in the droplet. For carrier liquids, such as xylene, benzene, and water, it is preferable to have temperatures less than their boiling points. Although less desirable, the present invention can be used with highly volatile carrier liquids, such as Freon. However, unless low temperatures are introduced, problems can arise with the rapid vaporization of the Freon removing solutes to the gaseous medium. In general, for a given solvent, the lower the temperature, the lower the rate of evaporation and the longer the tubular electrode 28 must be to accomplish complete evaporation of the solvent. On the other hand, if temperatures are too high, heat sensitive particles can be damaged, non-uniform or incomplete coating may occur, and there may be some loss of charge. Consequently, the electrostatic arrangement of the invention allows sufficient time for evaporation to occur at a desired rate, so as to prevent solute losses, but assuring complete solvent evaporation. Although not essential, by controlling the rate of evaporation, the charge remaining on the particle will be substantially equal to that originally placed on the droplet.

Droplet vaporation process at moderate temperatures is well understood and is described by basic equations that are obtained from energy and mass conservation principles. In addition to the temperature, evaporation is also controlled by the rate of diffusion of the vapor in the gaseous medium. In general, the mass flux varies directly with the diffusion coefficient in the stagnant gas medium and the vapor concentration and inversely with the droplets radius. Due primarily to collisions between molecules and molecules returning to the droplet's surface, the evaporation rate will fall short of the rate of phase transition. The net evaporation rate is equal to the rate of phase transition only in a vacuum and then only if the dimensions of the droplet's surface is less than about half the mean free path (on the order of 0.1 microns) in the corresponding equilibrium vapor or if a condensing surface is placed very close to the evaporating surface. As will be explained hereinafter, the use of a partial vacuum, although possible, is generally not preferred in the invention and the close positioning of a condensing surface is not possible. However, the small dimensions of the droplets greatly assist the net rate of evaporation. In the embodiment of FIG. 1, the water vapor from the evaporating droplets can readily escape from the open top and open bottom of the tubular electrode 28. Generally, conventional techniques where water vapor is pumped out of an enclosed volume are not necessary due to the relatively small quantities of water which is being evaporated during a given operational run. Moreover, it is desirable to avoid air flows within the tubular electrode 28, due to the small size of the dried particles. However, since sorting of the particles according to their mobility in an electrostatic field is not undertaken in the embodiment of FIG. 1, the open ends of the tubular electrode 28 are tolerable, since small air turbulences, although preferably avoided, do not greatly impair the operation of the apparatus 2. However, to avoid any substantial air turbulance that can impair results, the apparatus can be, if needed, completely enclosed during short operating cycles, with the water vapor being evacuated after each operational run. The length of a run can be extended by using a conventional liquid absorbent to control the vapor concentration in the gas surrounding the liquid droplets. Moreover, depending upon the vapor, there are known salts that will react with the vapor to form a compound having an extremely low vapor pressure. For instance, with water vapor, a suitable salt which may be used is anhydrous calcium sulfate. As the vapors reach the salt, they are removed from the gas medium. Although these techniques provide an inexpensive way of lengthening the time for continuous processing of droplets between operation stoppages for removing the saturated gas medium, unacceptable water vapor concentrations can be accumulated in the manner of a few minutes in a closed system. Hence, as will be described hereinafter, where longer continuous processing is desired, condensation techniques without air flows can be achieved.

Figure 6:
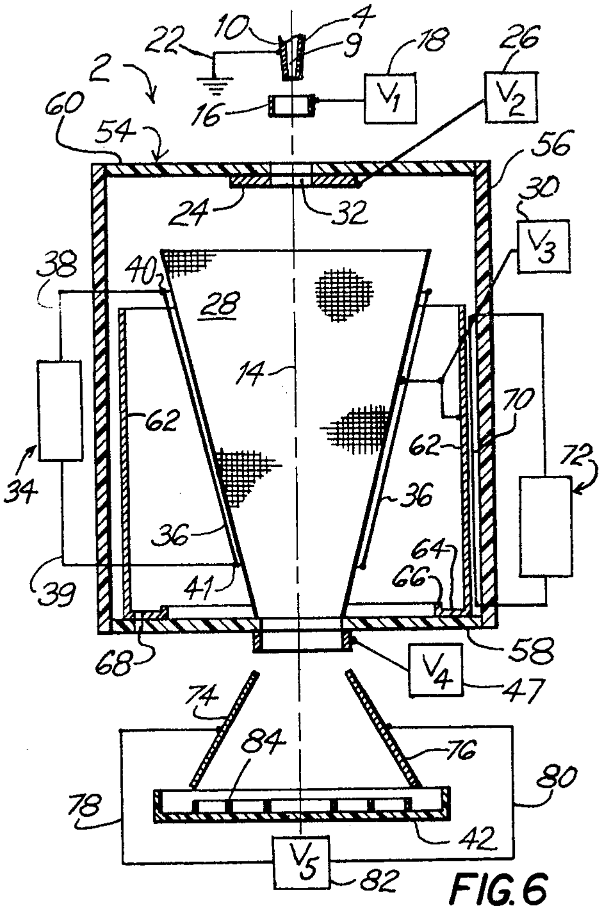
FIG. 6 is a cross-sectional view of yet another modification to the embodiment of FIG. 1.

Referring to FIG. 6, the apparatus 2 is enclosed in a housing 54, formed of a heat insulating, dielectric material, such as fiberglass. The housing 54 has a cylindrically shaped sidewall portion 56 with a pair of opposed end portions 58 and 60 mounted at each end thereof. The ring electrode 24 is mounted to the underside of the end portion 58 and the tubular electrode 28 is rigidly supported by the end portion 60. The tubular electrode 28 is formed of a metal wire mesh having holes of sufficient dimensions to allow water vapor to escape, while maintaining a radially symmetric electrostatic field. A metal condenser cylinder 62 is positioned in adjacent, spaced-apart relationship to the housing 54. The cylinder 62 has a ledge portion 64 with an upward turned flange portion 66 at the outer extremeties thereof. A drain tube 68 passes through the ledge portion 64 and the end portion 60. A cooling coil 70 is positioned behind the condenser cylinder 62 and carries coolant gas from a conventional refrigerant means 72. In operation, a substantial portion of the escaping vapor passes through the mesh tubular electrode 28, impinges upon the condenser cylinder 62, and condenses thereon. The collected water in the ledge portion 64 passes through drain tube 68. The condenser cylinder 62 is preferably held to the same voltage as the tubular electrode 28. This water vapor removing arrangement has been found to be particularly advantageous when the sorting of particles is undertaken and a substantial quantity of sample is to be processed. It is this type of situation wherein air movement needs to be greatly minimized and water vapor buildup in chamber during a relatively long run can be substantial. Therefore, as one possibility, the embodiment of FIG. 6 is shown with the circular electrode 45 mounted to the end portion 60 and a pair of oppositely charged, metal deflector plates 74 and 76. A potential difference is impressed between the plates 74 and 76 through a pair of electrical conductors 78 and 80, respectively, by a fifth voltage source 82. A plurality of parallel particle collectors 84 are horizontally aligned below the plates 74 and 76 to receive the particles, which are primarily sorted on the basis of their size and mass in the electrostatic field between the plates 74 and 76.

With the sorting feature of the embodiment of FIG. 6, the particles can be sorted primarily on the basis of their size, since each particle has about the same residual charge. Since the original droplet sizes are uniform in size, particles of the same size will be coated with substantially the same amount of coating material.

As will be obvious to those skilled in the art, it is possible to slightly increase the electrical forces acting on the charged droplets and particles by increasing the gas pressure. However, the economic costs normally do not justify these type of improvements. Likewise, by decreasing the gas pressure, more rapid evaporation can occur. Also, if substantial reduction in gas pressure is undertaken to create a partial vacuum, problems with eddy air flows, caused by the introduction of the droplets is greatly reduced. This can result in more accurate sorting of particles; however, it is generally not cost effective. Moreover, much more rapid heat input through microwave and infrared radiation is required to prevent freezing and to maintain the high rate of evaporation that occurs in a high vacuum. Moreover, it is known that at sufficiently high rates of evaporation, solutes will be removed, causing a loss in charge and incomplete coating. Also, the drag created by the gas medium, which is largely a function of gas viscosity, although initially somewhat insensitive to small decreases below atmospheric pressure, will be reduced at higher vacuums. In general, unless very accurate particle sorting is desired, based upon difference in particles' masses, a particle vacuum is not cost effective.

Numerous electrostatic arrangements, other than those shown in the present invention, are disclosed and shown in the parent application, Ser. No. 101,758, filed Dec. 10, 1979. These other electrostatic arrangements are also useable with the particle coating techniques of the present invention, and the entire parent application is incorporated by reference herein. Several of these arrangements have a center axis for the tubular electrode which is horizontally aligned, requiring the second electrode to be positioned to accelerate the particles and overcome air drag.

Optionally, depending upon the use of the apparatus 2 of the invention, a conventional particle scanning means, as shown in U.S. Pat. Nos. 3,380,584 and 3,710,933 can be included for automatically analyzing the suspended particles in a conventional flow chamber (not shown) of the scanning means to detect preselected physical or chemical characteristics of each particle by use of optical and/or impedance measurements. The conventional flow chamber wherein the optical or impedance measurements are taken, is positioned upstream of the nozzle 10 and generally would be positioned inside of the casing of the droplet forming means 4. In such a case, there would be two modes of operation of the charging collar electrode 16. In the previously described first mode, all of the droplets 12 can be uniformly charged. In the first mode of operation, the particle scanning means is not used. In other words, the collar electrode 16 is continuously at its charging voltage, without interruption. If the optical or impedance measurements are performed on the particles in the optional particle scanning means, in a second mode of operation the charging of a preselected subpopulation of particles can be accomplished in a manner illustrated in U.S. Pat. No. 3,380,584 to Fulwyler. Those droplets containing particles having detected parameters that fall within a predetermined subpopulation are charged with a substantially higher voltage than the remaining droplets. For example, 100 micron diameter droplets falling within the desired subpopulation can be charged with $10^{-12}$ Coulombs, whereas the remaining droplets are charged with one-tenth of that charge. Having all droplets charged to at least some extent prevents coalescence of droplets or clustering of dried particles. The charging of droplets in differing amounts, allows for the droplets to be sorted based upon the charge applied thereto, regardless of particle size. Optionally, a grounded metal disk (not shown) which acts as an electrostatic shield and has a center hole therein, can be positioned under the collar ring electrode 16.

The other electrostatic field arrangements shown in the copending parent application to this case can also be used with this invention and this invention should be viewed as a specific application of those apparatuses.

Although particular embodiments of the invention have been shown and described here, there is no intention to thereby limit the invention to the details of such embodiments. On the contrary, the intention is to cover all modifications, alternatives, embodiments, usages and equivalents of the subject invention as fall within the spirit and scope of the invention, specification and the appended claims.

What is claimed is:

1. An evaporator apparatus for coating individual particles with a coating material, the apparatus comprising:

means for suppling a liquid mixture of said particles, said coating material and a carrier liquid;

droplet forming means for forming a plurality of liquid droplets from said liquid mixture;

charging means for electrically charging said droplets proceeding from said droplet forming means;

temperature regulating means for controlling the temperatures within a predetermined spacial region; and electrode means for controlling the rate of movement of said evaporating droplets to allow completion of the evaporation of said carrier liquid while said droplets are within said predetermined region;

whereby the evaporation of said carrier liquid encapsulates said particles with said coating material.

2. The evaporator apparatus of claim 1, wherein said tubular electrode comprises a mesh; and said evaporator apparatus further comprising;

a cooled condenser surface disposed to receive and condense the vapor from the droplets.

3. The evaporator apparatus of claim 1, wherein said droplet forming means is adapted to form droplets with no more than one particle in each droplet, whereby each said particle is individually isolated so as to be encapsulated with a relatively uniform coating of a predetermined amount of coating liquid.

4. The evaporator apparatus of claim 3, wherein said temperature regulating means includes heat input means for increasing the rate of evaporation of said droplets.

5. The evaporator apparatus of claim 3, wherein said coating material comprises a polymerizable material.

6. The evaporator apparatus of claim 3, wherein said coating material comprises a resin.

7. The evaporator apparatus of claim 3, wherein said coating material forms an adhesive coating after drying.

8. The evaporator apparatus of claim 3, wherein said coating material forms a transparent coating after drying.

9. The evaporator apparatus of claim 3, wherein said particles comprise biological cells.

10. The evaporator apparatus of claim 3, further comprising, means for electrostatic sorting of the dried particles, proceeding from said tubular electrode, based upon said particles' sizes;

whereby formation of uniformally sized droplets provide substantially equal amounts of coating material to sorted, same sized droplets.

11. The evaporator apparatus of claim 3 wherein said electrode means comprises, a tubular electrode being adapted to receive said droplets after said droplets have been charged;

a second electrode being positioned substantially at one end of said tubular electrode;

means for impressing a potential difference between said tubular electrode and said second electrode to apply a charge of the same polarity as said charged droplets to said tubular electrode and a charge of the opposite polarity to said second electrode, whereby said tubular electrode exerts a repelling force and said second electrode exerts an attractive force on said droplets.

12. The evaporator apparatus of claim 11 wherein said tubular electrode has a center axis, said second electrode comprises a first ring electrode disposed in surrounding relationship to said center axis at an end of the tubular electrode which is adjacent the droplet forming means.

13. The evaporator apparatus of claim 12 wherein said tubular electrode has an inner surface with a circular cross section that is symmetrical about said center axis; said droplet forming means being positioned so that said droplets are provided with an initially linear trajectory that is substantially colinear with said center axis; said center axis of said tubular electrode is substantially vertically disposed.

14. The evaporator apparatus of claim 12 further comprising:

a third electrode being disposed at the end of said tubular electrode which is opposed to the end adjacent to said first ring electrode;

means for providing a potential difference between said tubular electrode and said third electrode to apply a charge to said third electrode of opposite polarity to that of the charged droplets; whereby the particles are retarded while being large and heavy, but are accelerated along said center axis after becoming small and light.

15. The evaporator apparatus of claim 14 wherein said third electrode traverses said center axis, whereby particles, which can be very small, will leave said tubular electrode and proceed toward said third electrode.

16. The evaporator apparatus of claim 14 wherein said third electrode comprises a second ring electrode disposed in surrounding relationship to said center axis, whereby the particles will pass through said ring electrode to be subsequently collected.

17. The evaporator apparatus of claim 14 wherein said third electrode comprises a funnel; said funnel being held to ground potential, whereby said particles, after being coated, lose their charge to said funnel, fall through said funnel to be subsequently examined or collected.

18. The evaporator apparatus of claim 17, further comprising, illuminating means for traversing the particles falling from said funnel with a beam of light;

optical detection means for detecting characteristics of the particles.

19. A method of coating particles comprising the steps of:

providing a liquid mixture of the particles, a coating material and a carrier liquid;

forming a plurality of liquid droplets from the liquid mixture so as to normally have no more than one particle in each droplet;

evaporating the carrier liquid from each airbourne droplet so that the coating material encapsulates the particle.

20. The method of claim 19, further including, charging the droplets;

steering the droplets with an electrostatic field so that the droplets proceed at a sufficient rate of movement to allow completion of the evaporation of the droplets within a predetermined region.

21. The method of claim 20, further including, controlling the temperatures to which the droplets are exposed, whereby the rate of evaporation is controlled.

* * * * *